United States Patent
Yamamoto (10) Patent No.: US 8,041,100 B2
(45) Date of Patent: Oct. 18, 2011

(54) SYSTEM FOR SPECIFYING EQUIPMENT CAUSING FAILURE

(75) Inventor: Toshio Yamamoto, Nara-ken (JP)

(73) Assignee: Sharp Kabushiki Kaisha, Osaka (JP)

( * ) Notice: Subject to any disclaimer, the term of this patent is extended or adjusted under 35 U.S.C. 154(b) by 377 days.

(21) Appl. No.: 12/226,606

(22) PCT Filed: Apr. 24, 2007

(86) PCT No.: PCT/JP2007/058832
§ 371 (c)(1), (2), (4) Date: Apr. 3, 2009

(87) PCT Pub. No.: WO2007/123238
PCT Pub. Date: Nov. 1, 2007

(65) Prior Publication Data
US 2009/0304259 A1 Dec. 10, 2009

(30) Foreign Application Priority Data
Apr. 25, 2006 (JP) .................. 2006-120421

(51) Int. Cl.
*G06K 9/00* (2006.01)
(52) U.S. Cl. ...................................... 382/141
(58) Field of Classification Search .................. None
See application file for complete search history.

(56) References Cited

U.S. PATENT DOCUMENTS 7,433,508 B2 * 10/2008 Sakai et al. .................. 382/144
7,813,539 B2 * 10/2010 Shibuya et al. ............... 382/141

FOREIGN PATENT DOCUMENTS

| JP | 10-326816 | 12/1998 |
| JP | 11-045919 | 2/1999 |
| JP | 2005-197629 | 7/2005 |
| JP | 2005-346596 | 12/2005 |

OTHER PUBLICATIONS

International Search Report, Jun. 12, 2007, issued in PCT/JP2007/058832.

* cited by examiner

*Primary Examiner* — Tu Nguyen
(74) *Attorney, Agent, or Firm* — Edwards Angell Palmer & Dodge LLP; David G. Conlin (57) ABSTRACT

A first defect distribution superimposed image is formed by superimposing defect distributions on individual substrates processed by a causal equipment unit candidate on one another. Second defect distribution superimposed images are formed by superimposing, on one another, defect distributions on individual substrates processed by equipment units other than the causal equipment unit candidate in one same step as that executed by the causal equipment unit candidate. The first defect distribution superimposed image and the second defect distribution superimposed images are displayed in contrast on one display screen.

5 Claims, 7 Drawing Sheets

| | MAP SUPERIMPOSITION | CLASSIFIED SUBSTRATE COUNT | DEFECT COUNT SUBSTRATE AVERAGE | STEP NO. | STEP NAME | EQUIPMENT UNIT NO. | PROBABILITY VALUE (p-value) |
|---|---|---|---|---|---|---|---|
| 37 | ⦿ | 30 | 60 | 20000 | PHOTO STEP | BBB-NO. 4 UNIT | 0.90 |
| | | | | 30000 | ETCHING STEP | CCC-NO. 4 UNIT | 0.80 |
| | | | | 10000 | DEPOSITION STEP | AAA-NO. 4 UNIT | 0.70 |
| 38 | ○ | 10 | 30 | 20000 | PHOTO STEP | BBB-NO. 1 UNIT | 0.80 |
| | | | | 10000 | DEPOSITION STEP | AAA-NO. 2 UNIT | 0.70 |
| | | | | | | | |
| 39 | ○ | 5 | 40 | | | | |
| | | | | | | | |
| | | | | | | | |
| 40 | ○ | 3 | 120 | 30000 | ETCHING STEP | CCC-NO. 3 UNIT | 0.70 |
| | | | | | | | |
| | | | | | | | |
| 41 | ○ | 3 | 70 | | | | |
| | | | | | | | |
| | | | | | | | |

1ST CANDIDATE / 2ND CANDIDATE / 3RD CANDIDATE

STEP: 20000   PHOTO STEP   EQUIPMENT UNIT NO.: BBB-NO. 4 UNIT   PROBABILITY VALUE: 0.90

| EQUIPMENT UNIT NO. | BBB-NO. 4 UNIT | BBB-NO. 1 UNIT | BBB-NO. 2 UNIT | BBB-NO. 3 UNIT | BBB-NO. 5 UNIT | BBB-NO. 7 UNIT | BBB-NO. 8 UNIT | BBB-NO. 9 UNIT |
|---|---|---|---|---|---|---|---|---|
| SUBSTRATE MAP SUPERIMPOSITION | | | | | | | | |
| PROCESSED ESTIMATED SUBSTRATE COUNT | 20 | 0 | 1 | 0 | 1 | 1 | 5 | 2 |
| PROCESSED SUBSTRATE COUNT | 50 | 5 | 4 | 3 | 3 | 4 | 80 | 82 |
| % | 40.00 | 0 | 25.00 | 0 | 33.33 | 25.00 | 6.25 | 2.43 |

Fig.5A

ANNULAR TYPE

Fig.5B

CRACK-SHAPE TYPE

Fig.5C

SHORTER-SIDE OPPOSITE-ENDS TYPE

| LOT ID | SUBSTRATE ID | STEP NUMBER | DEFECT SIZE 1 | COORDINATE x1 | COORDINATE y1 | DEFECT SIZE 2 | COORDINATE x2 | COORDINATE y2 | ... | DEFECT SIZE (n) | COORDINATE x(n) | COORDINATE y(n) |
|---|---|---|---|---|---|---|---|---|---|---|---|---|
| AAA00001 | AAA00001-1 | 30000 | S | 100 | 200 | M | 110 | 200 | | S | 900 | 800 |
| AAA00001 | AAA00001-2 | 30000 | M | 120 | 100 | M | 130 | 110 | | L | 880 | 830 |
| AAA00001 | AAA00001-3 | 30000 | S | 180 | 120 | L | 180 | 130 | | M | 890 | 850 |
| AAA00001 | AAA00001-4 | 30000 | L | 110 | 130 | M | 120 | 140 | | L | 910 | 920 |
| AAA00001 | AAA00001-5 | 30000 | M | 120 | 100 | S | 130 | 140 | | S | 830 | 910 |
| .. | .. | .. | .. | .. | .. | .. | .. | .. | | .. | .. | .. |

Fig.8

| LOT ID | SUBSTRATE ID | STEP NUMBER | PROCESSING EQUIPMENT UNIT | PROCESSING DATE |
|---|---|---|---|---|
| AAA00001 | AAA00001-1 | 10000 | AAA-NO. 1 UNIT | 2005/01/01 10:10:00 |
| AAA00001 | AAA00001-1 | 20000 | BBB-NO. 2 UNIT | 2005/01/02 10:10:00 |
| AAA00001 | AAA00001-1 | 50000 | CCC-NO. 1 UNIT | 2005/01/03 10:10:00 |
| AAA00001 | AAA00001-2 | 10000 | AAA-NO. 2 UNIT | 2005/01/04 10:10:00 |
| AAA00001 | AAA00001-2 | 20000 | BBB-NO. 3 UNIT | 2005/01/05 10:10:00 |
| .. | .. | .. | .. | .. |

SYSTEM FOR SPECIFYING EQUIPMENT CAUSING FAILURE

TECHNICAL FIELD

The present invention relates to failure-cause equipment determination systems and, more specifically, to a system for determining an abnormal step or equipment unit that causes a product failure or the like in a production line including a plurality of steps.

BACKGROUND ART

Conventionally, in multi-step production lines for semiconductor devices, thin film devices and the like, various in-line inspections are performed with a view to achieving improvement of product quality and stabilization of equipment, and there is introduced a system for determining an abnormal step or equipment unit that causes a product failure or the like based on inspection information acquired by the in-line inspections. For example, JP 2005-197629 A discloses a technique that defect distribution states of product substrates are classified based on information acquired by a pattern defect inspection, which is one of the in-line inspections, followed by performing common path analysis as to the similarity level of the defect distribution states by using production history information, by which problematic equipment candidates are specifically determined.

In the technique of JP 2005-197629 A, a report display screen is presented to report a user on the result of determination of problematic equipment candidates. This report display screen contains information (product type, lot number, inspection date, etc.) for identifying abnormality-detected inspected wafers, inspection information (defect distribution images) as to those wafers, information (device name, etc.) for identifying problematic equipment candidates, information (defect distribution images) from which the problematic equipment candidates have been identified, and information representing statuses (being problematic or not, countermeasure-taken or not) of the problematic equipment candidates.

DISCLOSURE OF INVENTION

Before a user takes a countermeasure to failure with a view to improving the yield in an actual production line, the user (including the operator of the system) would typically attempt to confirm by human judgment whether or not a problematic equipment candidate automatically determined by the system is really the cause of the abnormality. This is because, in case that a countermeasure to failure is taken based on erroneous information, it would cause the production line to incur an enormous loss.

However, the technique of JP 2005-197629 A, in which only insufficient information can be displayed on the report display screen, has an issue that the user has difficulty in judging whether or not the determined problematic equipment candidate is really the cause of abnormality.

For example, for the operator to confirm whether or not a determined problematic equipment candidate is really the cause of abnormality, it helps an easier understanding to compare, in contrast, in-line inspection information resulting from the use of the problematic equipment candidate and in-line inspection information resulting from the use of equipment units other than the problematic equipment candidate. However, in an attempt to make such a contrast with the technique of JP 2005-197629 A, it would be necessary for the operator to redo the retrieval of in-line inspection information, production history information, or the like as to the use of equipment units other than the problematic equipment candidate each time such a case has occurred. This would take enormous time and labor. In a case where this causes a delay of the introduction of a right countermeasure to failure, e.g., when intrusion of foreign matters into equipment units is the cause of the abnormality, the occurrence of failure would continue for some more time, incurring an enormous loss.

Accordingly, an object of the present invention is to provide a failure-cause equipment determination system for determining an abnormal equipment unit that causes a product failure or the like in a production line including a plurality of steps, the system allowing a user to promptly and easily judge whether or not an equipment unit determined by the system (hereinafter, referred to as causal equipment unit candidate) is really the cause of the abnormality.

In order to accomplish the object, the present invention provides a failure-cause equipment determination system for determining an equipment unit that has caused failure occurrence in a production line in which one or more steps are executed on substrates by using one or more equipment units that can execute the individual steps, respectively, wherein the production line includes an inspection step for acquiring defect distribution information representing positions of defects on each of the substrates after an end of specified steps, the system comprising:

a classification result acquisition section for classifying the substrates for each one of defect distribution patterns by using the defect distribution information as to the individual substrates;

a causal equipment candidate determination section for determining causal equipment unit candidates that have caused failure occurrence out of the plurality of equipment units based on a classification result acquired by the classification result acquisition section and production history information for determining equipment units that have processed the substrates in the individual steps, respectively;

a first defect distribution image forming section for forming a first defect distribution superimposed image by superimposing defect distributions on the individual substrates processed by the causal equipment unit candidates on one another;

a second defect distribution image forming section for forming a second defect distribution superimposed image by superimposing, on one another, defect distributions on individual substrates processed by each of equipment units other than the causal equipment unit candidate in one same step as that executed by the causal equipment unit candidate; and a first display section for displaying the first defect distribution superimposed image and the second defect distribution superimposed images in contrast on one display screen.

In the failure-cause equipment determination system of this invention, a first defect distribution superimposed image formed by superimposing, on one another, defect distributions on individual substrates processed by the causal equipment unit candidates, and a second defect distribution superimposed image formed by superimposing, on one another, defect distributions on individual substrates processed by equipment units other than the causal equipment unit candidates in one same step as that executed by the causal equipment unit candidates, are displayed in contrast on one display screen. Accordingly, whether or not causal equipment unit candidates determined by this system are really the cause of abnormality can be intuitively grasped by a user (including the system operator, which is applicable hereinafter) through the sense of vision and moreover judged more promptly and easily than it could conventionally.

The failure-cause equipment determination system of one embodiment, further comprises:

a third defect distribution image forming section for forming a third defect distribution superimposed image by superimposing, on one another, defect distributions on substrates classified into one defect distribution pattern; and a second display section for listing and displaying, for each one of the defect distribution patterns, a third defect distribution superimposed image corresponding to the defect distribution pattern, and causal equipment unit candidate information representing causal equipment unit candidates corresponding to the defect distribution pattern, together on the display screen.

In the failure-cause equipment determination system of this one embodiment, for each one of the defect distribution patterns, a third defect distribution superimposed image corresponding to the defect distribution pattern, and causal equipment unit candidate information representing causal equipment unit candidates corresponding to the defect distribution pattern, are listed and displayed together on the display screen. That is, the third defect distribution superimposed images and the causal equipment unit candidates are displayed in a list form in association with each other. Accordingly, the user is enabled to narrow down, based on past experiences as an example, causal equipment units that are really the cause of abnormality out of the causal equipment unit candidates determined by this system, more promptly and easily than it could conventionally.

In the failure-cause equipment determination system of this one embodiment, the second display section displays its display contents limitedly as to causal equipment unit candidates satisfying a specified threshold value for determination of causal equipment units out of the causal equipment unit candidates corresponding to the defect distribution pattern.

In the failure-cause equipment determination system of this one embodiment, causal equipment unit candidate information to be displayed by the second display section is limited to causal equipment unit candidates satisfying a specified threshold value for determination of causal equipment units out of the causal equipment unit candidates corresponding to the defect distribution pattern. That is, causal equipment unit candidates that do not satisfy the specified threshold value for the determination of causal equipment units out of the causal equipment unit candidates corresponding to the defect distribution pattern are determined as causal equipment units having low degrees of association, and omitted from display. Accordingly, the user is enabled to further promptly and easily narrow down causal equipment units that are really the cause of abnormality out of the causal equipment unit candidates determined by the system.

The failure-cause equipment determination system of one embodiment, further comprises:

an instruction input section for inputting an instruction to select one of causal equipment unit candidates of which causal equipment unit candidate information is displayed on the display screen, wherein the first display section, in linkage with a causal equipment unit candidate selected via the instruction input section, switches its display contents so as to display the first defect distribution superimposed image and the second defect distribution superimposed images as to the selected causal equipment unit candidate.

In the failure-cause equipment determination system of this one embodiment, the operator is allowed, for example, via the instruction input section to select any one of the causal equipment unit candidates as to which causal equipment unit candidate information is displayed on the display screen. In this system, when one of the causal equipment unit candidates is selected in this way, the first display section, in linkage with a causal equipment unit candidate selected via the instruction input section, switches its display contents so as to display the first defect distribution superimposed image and the second defect distribution superimposed image as to the selected causal equipment unit candidate. Accordingly, without the operator's redoing the retrieval of inspection information, production history information, or the like associated with the use of equipment units other than the causal equipment unit candidates each time, a first defect distribution superimposed image formed by superimposing, on one another, defect distributions on individual substrates processed by the selected causal equipment unit candidate, and a second defect distribution superimposed image formed by superimposing, on one another, defect distributions on individual substrates processed by equipment units other than the causal equipment unit candidate in one same step as that executed by the causal equipment unit candidates, are displayed in contrast on the display screen. Accordingly, whether or not the selected causal equipment unit candidate is really the cause of abnormality can be intuitively grasped by the user through the sense of vision and moreover judged more promptly and easily than it could conventionally.

In the failure-cause equipment determination system of one embodiment, the first and second defect distribution image forming sections form the first and second defect distribution superimposed images, respectively, for each one of the equipment units based on information for identifying the substrates and the production history information.

In the failure-cause equipment determination system of this one embodiment, the first and second defect distribution image forming sections form the first and second defect distribution superimposed images, respectively, for each one of the equipment units. As a result, whether or not causal equipment unit candidates determined by this system are really the cause of abnormality can be intuitively grasped and moreover judged more promptly and easily, for each one of the equipment units, by the user through the sense of vision.

BEST MODE FOR CARRYING OUT THE INVENTION

Hereinbelow, the present invention will be described in detail by way of embodiment illustrated in the accompanying drawings.

Figure 1:
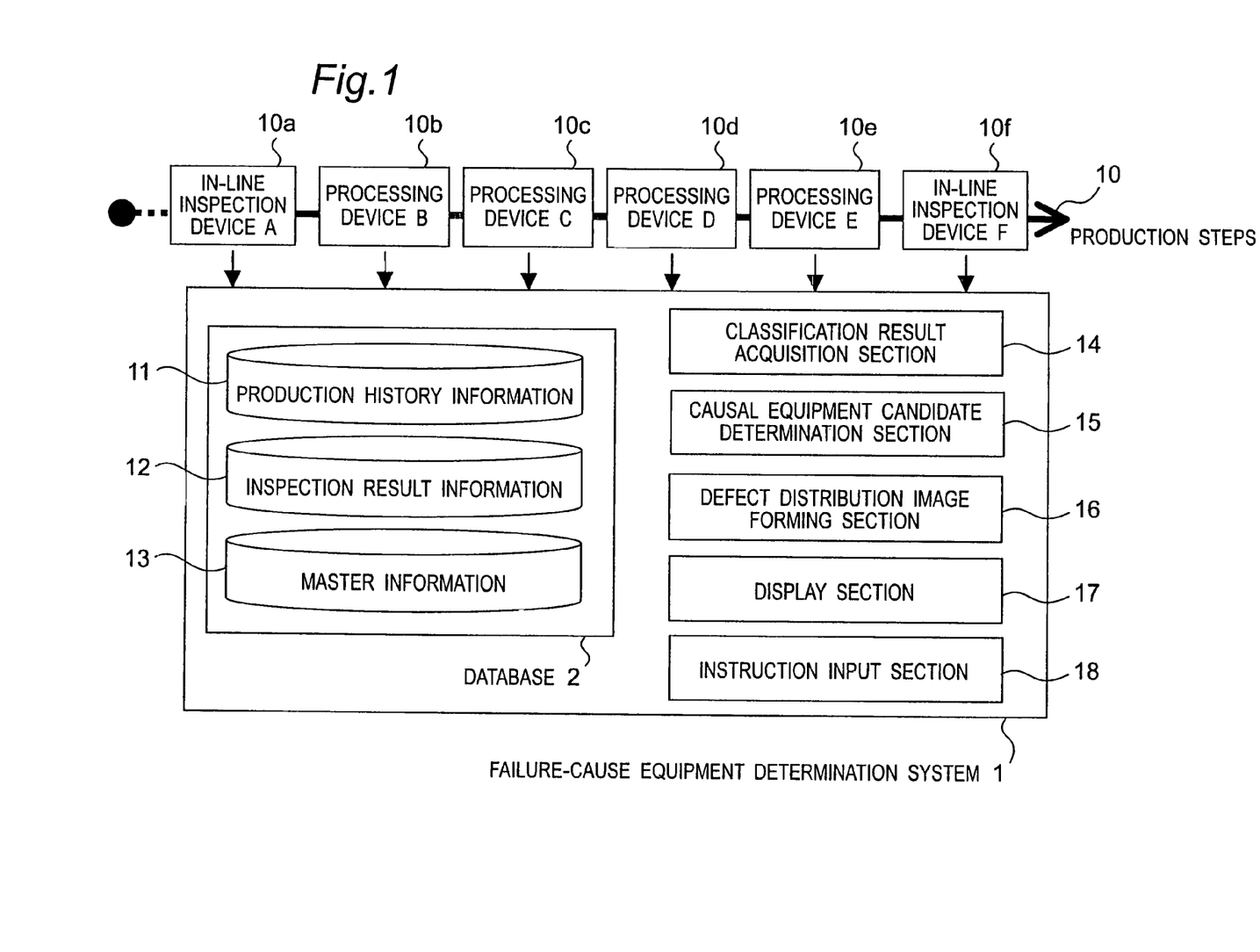
FIG. 1 shows a schematic block diagram of a failure-cause equipment determination system according to an embodiment of the present invention as well as a production line to which the failure-cause equipment determination system is applied.

FIG. 1 illustrates a block diagram of a failure-cause equipment determination system 1 according to an embodiment of the invention as well as a production line 10 of thin film devices to which the system is applied.

Generally, a production line of thin film devices or semiconductor devices is composed of multiple steps, from reception of substrates to completion of devices, to be executed sequentially on production lot by production lot basis.

Part of such a thin film device production line 10 is shown in FIG. 1. In this example, the production line 10 includes an inspection step 10a with use of an in-line inspection device A, a step 10b with use of a processing device B, a step 10c with use of a processing device C, a step 10d with use of a processing device D, a step 10e with use of a processing device E, and an inspection step 10f with use of an in-line inspection device F. That is, the processing steps 10b, 10c, 10d, 10e refer to processing steps such as a cleaning step for cleaning a substrate as an example, a film deposition step (hereinafter, referred to as "deposition step") for forming a thin film on the substrate, a photolithography step (including exposure step, development step, etc.; hereinafter, referred to as "photo step") for forming a pattern of photoresist on the thin film, and an etching step for patterning the thin film with the photoresist used as a mask. The processing device B, the processing device C, the processing device D, and the processing device E each denote a plurality of equipment units, collectively. That is, it is assumed that in XXX step as an example, a plurality of equipment units referred to as XXX-No. 1 unit, XXX-No. 2 unit, respectively, are used.

Figure 5A:
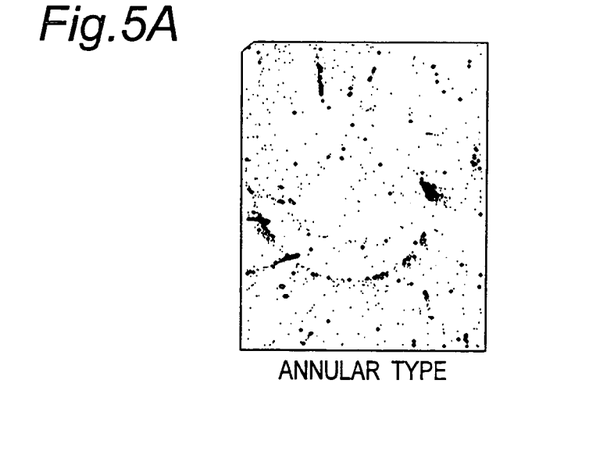
FIG. 5A is a view showing an example of an annular type defect distribution occurring on a substrate surface.
Figure 5B:
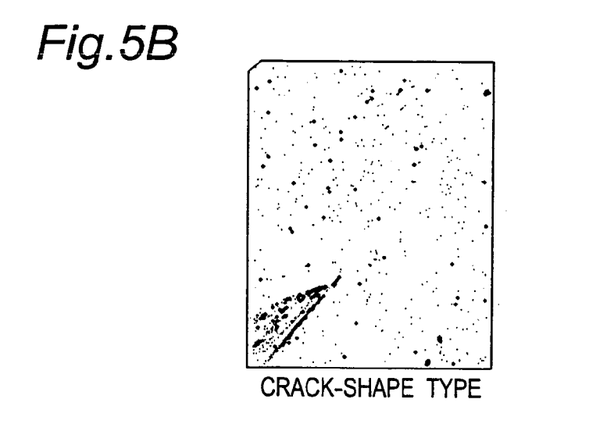
FIG. 5B is a view showing an example of a crack-shape type defect distribution occurring on a substrate surface.
Figure 5C:
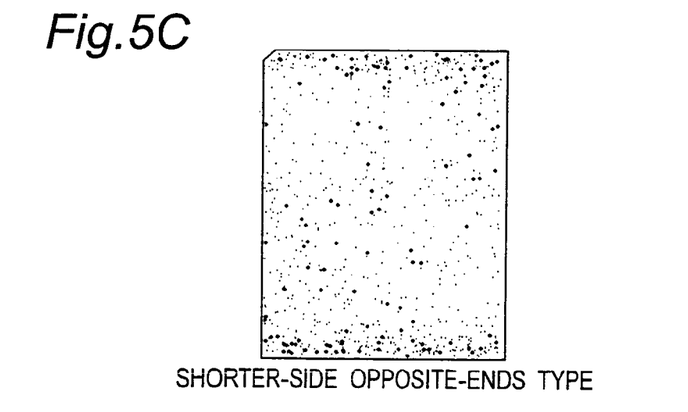
FIG. 5C is a view showing an example of a shorter-side opposite-ends type defect distribution occurring on a substrate surface.

The inspection steps 10a, 10f are intended, in this example, to perform pattern defect inspections to acquire information representing positions and sizes of defects on the individual substrates as inspection result information. As defects on substrates, there may occur various defect distributions as shown in FIGS. 5A, 5B and 5C. FIG. 5A shows a pattern in which defects appear in an annular shape (annular type) on a substrate surface, FIG. 5B shows a pattern in which defects appear like a crack or chip (crack-shape type) on a substrate surface, and FIG. 5C shows a pattern in which defects appear so as to be concentrated along shorter sides of a substrate on the substrate surface (shorter-side opposite-ends type).

As shown in FIG. 1, the failure-cause equipment determination system 1 includes a database 2, a classification result acquisition section 14, a causal equipment candidate determination section 15, a defect distribution image forming section 16, a display section 17, and an instruction input section 18. The database 2 includes a production history information storage section 11 for storing production history information, an inspection result information storage section 12 for storing inspection result information, and a master information storage section 13.

Figure 2:
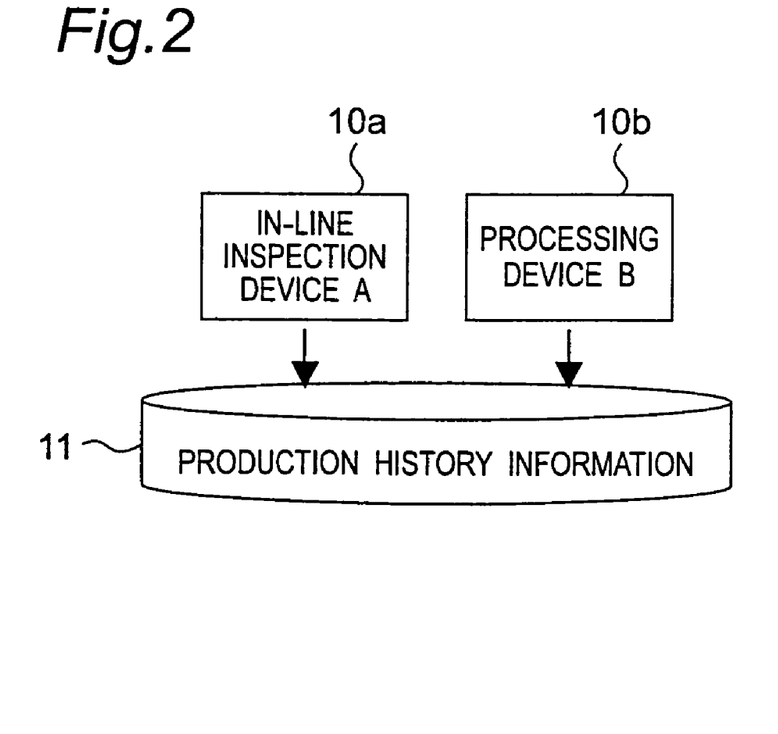
FIG. 2 is a view for explaining a way how production history information is stored in a production history information storage section.
Figure 8:
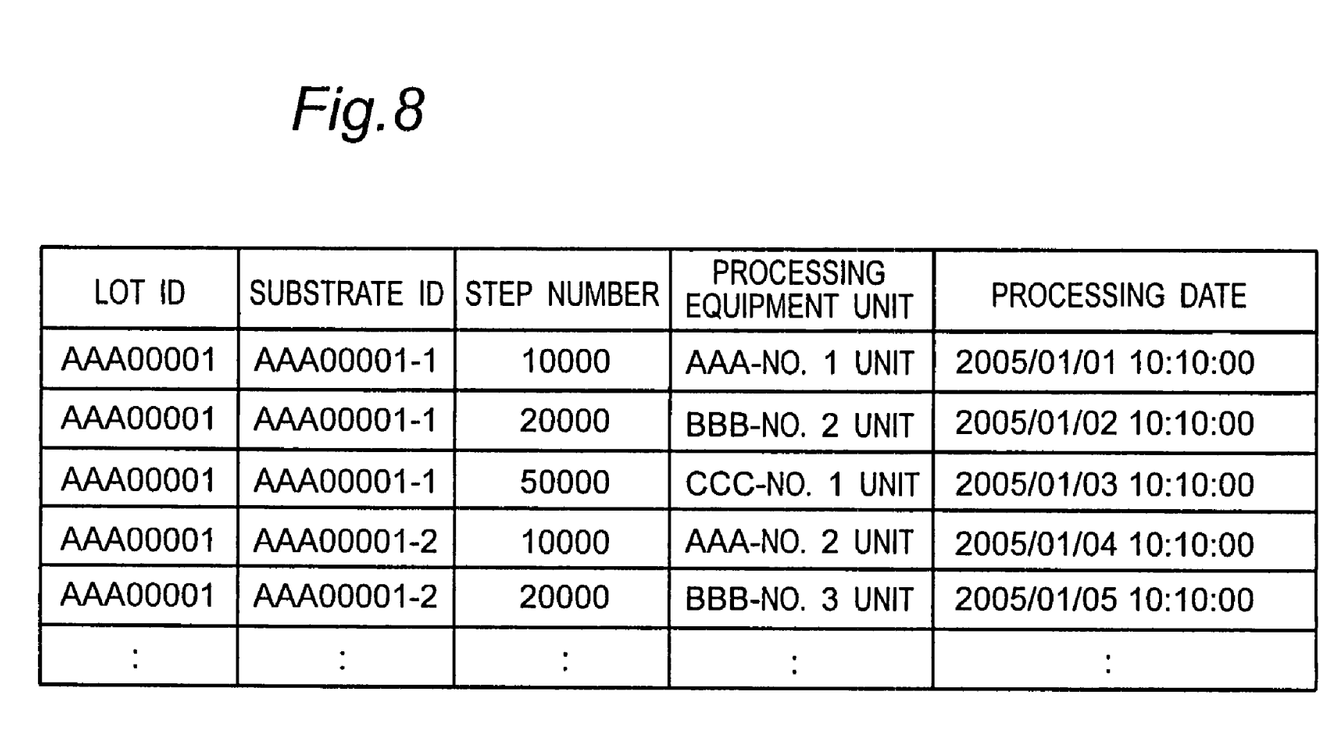
FIG. 8 is a chart showing a format of the production history information.

As illustrated in FIG. 2, production history information is stored in the production history information storage section 11 from the in-line inspection device A or the processing device B or the like, from time to time, in real time. The format of this production history information has, as shown in an exemplary table of FIG. 8, a lot number (lot ID) for identifying a production lot, a substrate number (substrate ID) for identifying a substrate, a step number for identifying a step, a unit number (processing equipment ID) for identifying an equipment unit used in one step, and a processing date, in association with one another. From this production history information, with respect to a substrate AAA00001-1 contained in a lot AAA00001 as an example, it can be seen that a step 10000 was executed at 10:10:00 on Jan. 1, 2005 by using a processing equipment unit AAA-1.

Figure 3:
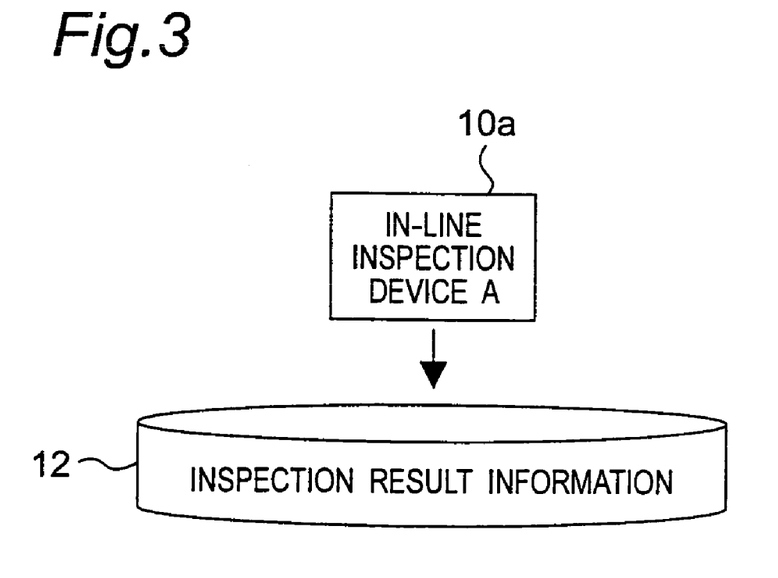
FIG. 3 is a view for explaining a way how inspection result information is stored in an inspection result information storage section.
Figure 7:
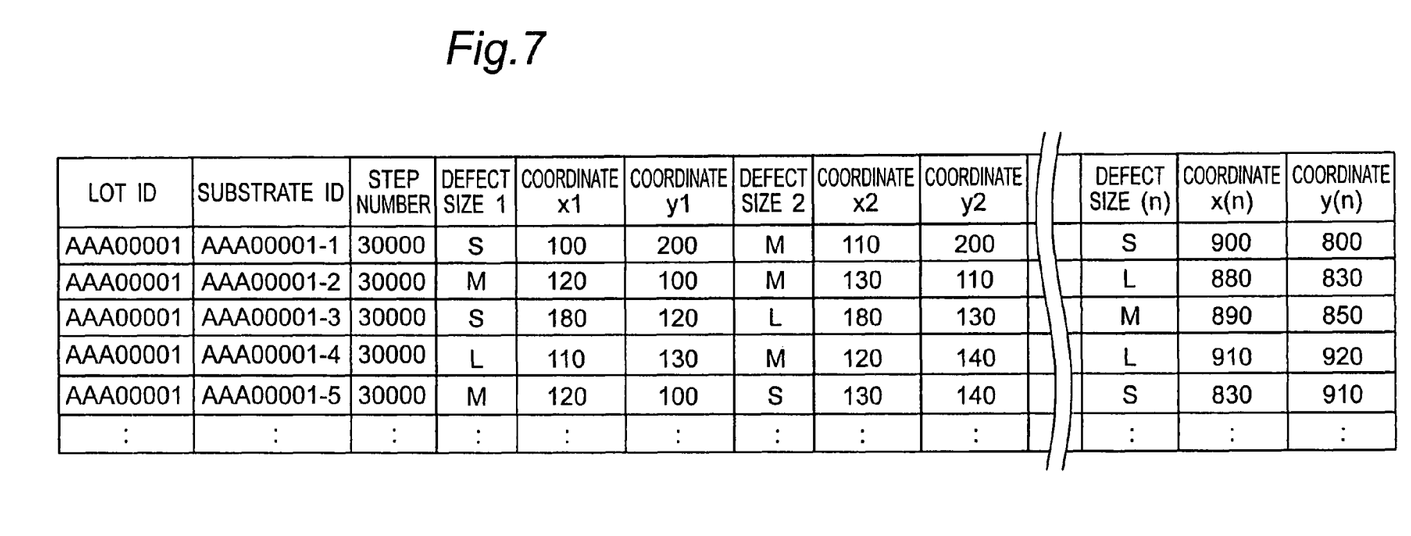
FIG. 7 is a chart showing a format of the inspection result information.

As illustrated in FIG. 3, defect distribution information as inspection result information, i.e. information representing positions and sizes of defects on the individual substrates, is stored in the inspection result information storage section 12 from the in-line inspection device A or the like, from time to time, in real time. The output form (format) of this defect distribution information, as shown in an exemplary table of FIG. 7, has a lot ID, a substrate ID, a step number, defect sizes representing sizes of individual defects (classified as small size S, middle size M, large size L), and xy-coordinates representing positions of the defects on the substrate surface, in association with one another. From this defect distribution information, with respect to the substrate AAA00001-1 contained in the lot AAA00001 as an example, it can be seen that in a step 30000, a size of a first defect is S, a x-coordinate of the defect is 100, a y-coordinate of the defect is 200, a size of a second defect is M, an x-coordinate of the defect is 110, a y-coordinate of the defect is 200, while a size of an n-th defect is S, an x-coordinate of the defect is 900, and a y-coordinate of the defect is 800.

Threshold values relating to the determination of causal equipment units by the causal equipment candidate determination section 15 are stored in the master information storage section 13 shown in FIG. 1.

The classification result acquisition section 14 classifies the substrates for each one of defect distribution patterns by using the defect distribution information as to the individual substrates. In this example, the classification result acquisition section 14 uses a known method that defect distribution information as to the individual substrates are compared with known defect distribution patterns serving as teaching data to calculate similarities between the defect distributions of the individual substrates and the known defect distribution patterns, where if a calculated similarity is equal to or greater than a certain threshold value, the substrate is classified into a relevant known defect distribution pattern. As the threshold value, the data stored in the master information storage section 13 shown in FIG. 1 are looked up and used. In addition, the defect distribution pattern classification method may be another classification method such as a method using independent component analysis for extracting/classifying characteristic patterns without using teaching data.

Based on the classification result acquired by the classification result acquisition section 14 and the production history information stored in the production history information storage section 11, the causal equipment candidate determination section 15 performs a common path analysis (an analysis for pursuing which equipment units have been used in common to process a plurality of substrates having similar defect distributions) to extract causal equipment units that have caused failure occurrence out of a plurality of equipment units.

The defect distribution image forming section 16 forms a plurality of kinds of defect distribution superimposed images by superimposing defect distributions (bit map images) on the individual substrates on one another (described later in detail).

The display section 17 displays information related to causal equipment unit candidates determined by the causal equipment candidate determination section 15, as a two-dimensional image, on one display screen such as a CRT (cathode-ray tube) or LCD (Liquid Crystal Display).

The instruction input section 18 is implemented by a mouse, a keyboard or the like and used to input a desired instruction to the system 1 by the operator.

As can be understood by those skilled in the art, such a system 1 can be implemented by a computer, more particularly, a personal computer. Operations of the individual sections 14, 15, . . . , 18 can be implemented by a computer program (software).

This system 1 operates according to the processing flow shown in FIG. 6 in the following manner.

First, at step S51, the classification result acquisition section 14 reads inspection result information, i.e. defect distribution information, as to the individual substrates from the inspection result information storage section 12. Subsequently, at step S52, the classification result acquisition section 14 classifies the substrates by using their defect distribution information for each one of the defect distribution patterns (automatic classification of patterns within the substrate surface).

Next, at step S53, the classification result acquisition section 14 extracts, for each defect distribution pattern, substrate IDs classified as matching the defect distribution pattern and substrate IDs not matching the defect distribution pattern. This allows the substrate IDs and the defect distribution patterns matching the substrate IDs to be associated with each other, respectively.

Next, at step S54, the causal equipment candidate determination section 15 reads the production history information from the production history information storage section 11. Subsequently, at step S55, the causal equipment candidate determination section 15 performs a common path analysis based on the classification result acquired by the classification result acquisition section 14 and the production history information read from the production history information storage section 11, thereby determining causal equipment unit candidates that have caused failure occurrence out of the plurality of equipment units. For determination of causal steps and causal equipment units, generally, data mining software is often used to do examinations and output results of the individual examinations. However, the part in which significant differences among the equipment units are evaluated by using production history information is dependent on the algorithm for pattern classification, and therefore either common path analysis may be used in this invention.

Next, at step S56, the defect distribution image forming section 16, serving as first, second and third defect distribution image forming sections, forms a plurality of kinds of defect distribution superimposed images by superimposing defect distributions (bit map images) on the individual substrates on one another. In this example, the first, second and third defect distribution superimposed images are formed depending on defect distributions of which substrates are superimposed. The first defect distribution superimposed image is a result of superimposing, on one another, defect distributions on substrates processed by causal equipment unit candidates in one step. The second defect distribution superimposed image is a result of superimposing, on one another, defect distributions on substrates processed by equipment units other than the causal equipment unit candidates in the same step as that executed by the causal equipment unit candidates. The third defect distribution superimposed image is a result of, for each one of the defect distribution patterns, superimposing defect distributions on substrates classified into the defect distribution pattern, on one another. In addition, in the method for performing the superimposition of images, color setting including transparency is applied to individual substrates so that even if the substrates are overlapped with one another, their defect information (defect size and position) is discriminable from one another.

Figure 6:
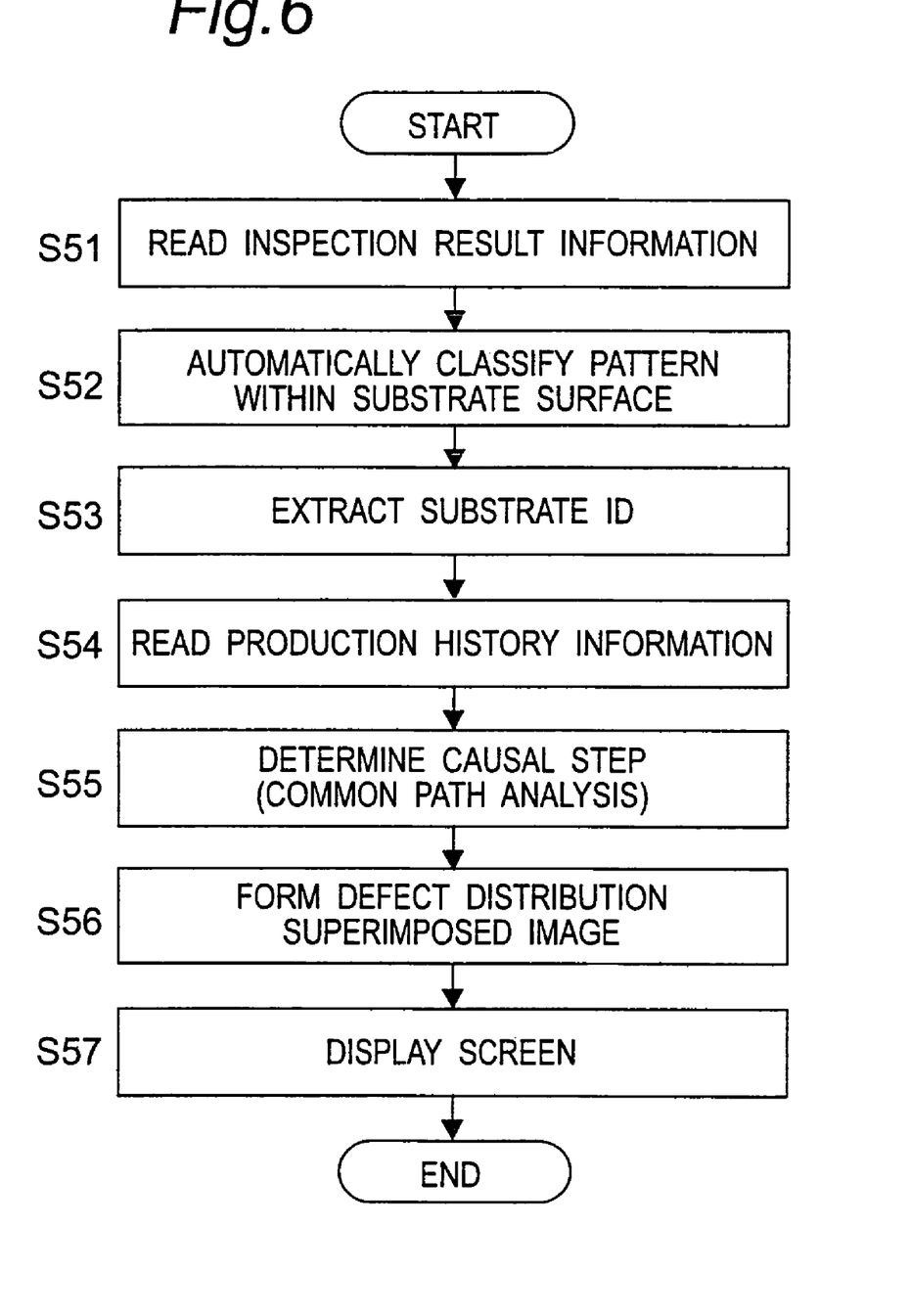
FIG. 6 shows an operation flow of the failure-cause equipment determination system.

Next, at step S57 in FIG. 6, the display section 17, serving as first and second display sections, displays information related to causal equipment unit candidates determined by the causal equipment candidate determination section 15 on one display screen implemented by CRT or LCD.

Figure 4:
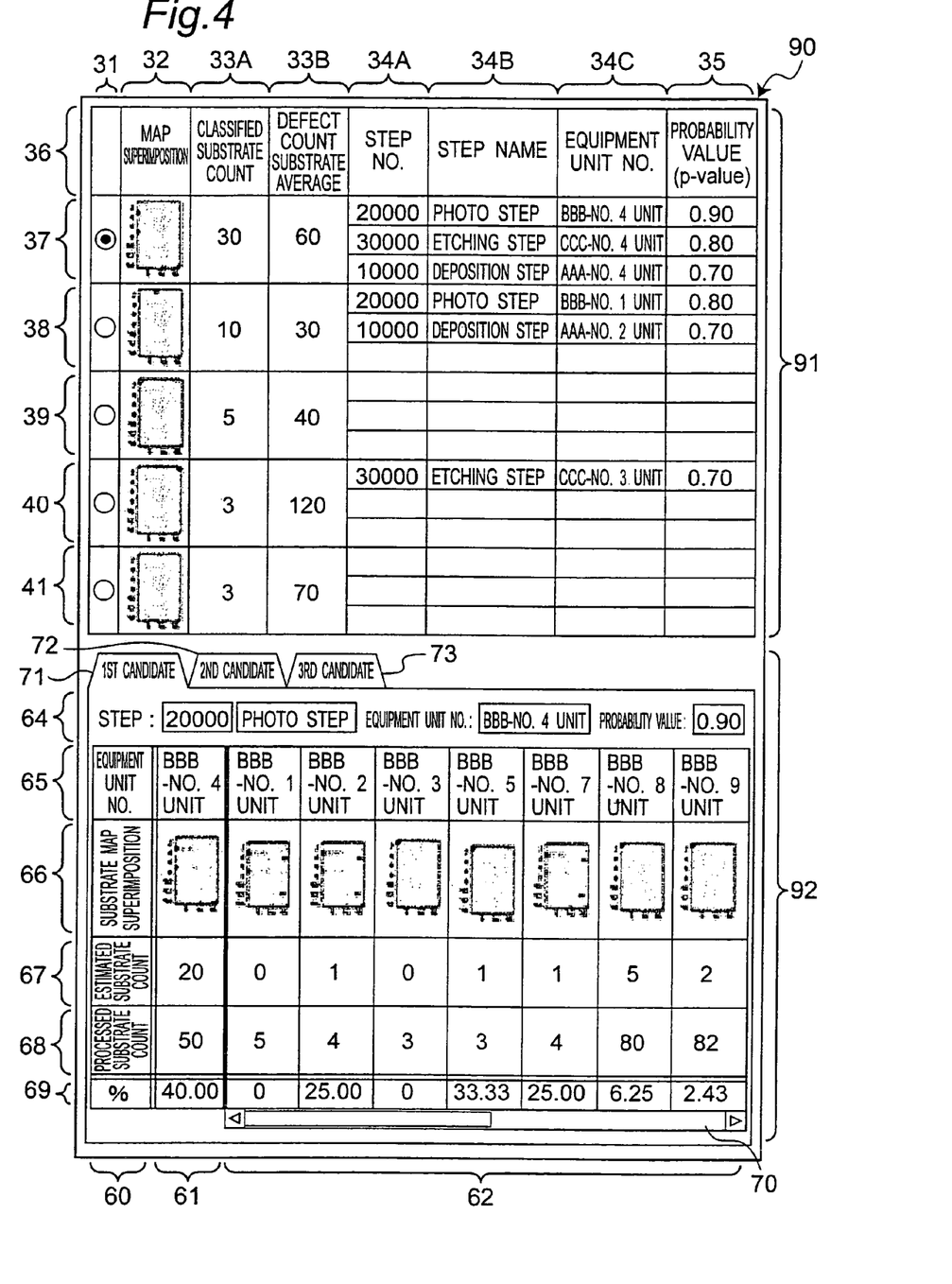
FIG. 4 is a view showing an example of a display screen displayed by the failure-cause equipment determination system.

FIG. 4 illustrates an aspect in which information as to causal equipment unit candidates determined by the causal equipment candidate determination section 15 is displayed on a display screen 90 by the display section 17 as a two-dimensional image containing the defect distribution superimposed map.

The display screen 90 of FIG. 4 is composed roughly of an upper table area 91 for displaying a classification result of defect distributions on substrates for each of the defect distribution patterns, and a lower table area 92 for displaying differences among equipment units (unit differences) in terms of defect distributions of substrates.

The upper table area 91 is longitudinally segmented into an item display area 36, and pattern classification areas 37, 38, 39, 40 and 41 representing classification results for each defect distribution pattern. Also, the upper table area 91 is laterally segmented into a check field 31 to be checked by an operator with an unshown mouse, a 'map superimposition' field 32 for displaying the third defect distribution superimposed image, a 'classified substrate count' field 33A for displaying a count of substrates classified into the corresponding defect distribution pattern, a 'defect count substrate average' field 33B for displaying an average value per substrate of the counts of defects classified into the defect distribution pattern, a 'step No.' field 34A representing step numbers, a 'step name' field 34B representing step names, an 'equipment unit No.' field 34C representing Nos. of cause candidate equipment units that have executed their corresponding steps, and a 'probability value (p-value)' field 35 representing probability values of corresponding cause candidate equipment units.

In this display example, for example, in the pattern classification area 37, it can be seen that the defect distribution pattern of this pattern classification area is the defect distribution superimposed image displayed in the map superimposition field 32 (an image in which defects appear concentrated at an upper left corner), the count of substrates classified into the defect distribution pattern is 30, and the defect count substrate average value is 60. Further, it can be seen that the determined causal equipment unit candidates are BBB-No. 4 unit, CCC-No. 4 unit, and AAA-No. 4 unit, and their probability values of being the cause of abnormality are 0.90, 0.80, and 0.70, respectively.

The check field 31 is provided in each of the pattern classification areas 37, 38, 39, 40 and 41. When the operator checks the check field 31 of one pattern classification area by using a mouse (not shown) as the instruction input section 18, information related to the checked pattern classification area is switchedly displayed in the lower table area 92 in linkage with the checking (described later).

In the pattern classification areas 37, 38, 39, 40 and 41, since defect distribution superimposed images are displayed in the map superimposition fields 32, respectively, the operator can intuitively grasp a defect distribution pattern for each one of the pattern classification areas through the sense of vision.

The third defect distribution superimposed images displayed in the map superimposition field 32 in the pattern classification areas 37, 38, 39, 40 and 41, respectively, are arrayed in an order of descending number of the classified substrate counts. This allows the operator to easily grasp more important defect distribution patterns.

Also in the pattern classification areas 37, 38, 39, 40 and 41, average values of defect counts per substrate are displayed in the 'defect count substrate average' field 33B. As a result, in a case where the number of defects occurring to each one substrate is small, even if an abnormal phenomenon related to one pattern classification area is classified into a characteristic defect distribution pattern, it would be appropriate that the user lower the priority of the countermeasure (yield improvement action) for the abnormal phenomenon.

Also in the pattern classification areas 37, 38, 39, 40 and 41, unit numbers of cause candidate equipment units determined by the causal equipment candidate determination section 15 are displayed in the 'equipment unit No.' field 34C. In the 'step No.' field 34A and the 'step name' field 34B are displayed step numbers and step names executed by corresponding cause candidate equipment units, respectively. These are displayed in association with the third defect distribution superimposed images displayed in the map superimposition field 32. That is, for each one of the pattern classification areas 37, 38, 39, 40 and 41, a third defect distribution superimposed image classified into a defect distribution pattern and causal equipment unit candidate information representing causal equipment unit candidates corresponding to the defect distribution pattern are displayed in a list form in association with each other. Accordingly, the user is allowed to easily judge whether or not the causal equipment unit candidate is really the cause of abnormality.

For example, when such an annular type defect distribution as shown in FIG. 5A has occurred, a spin-related processing device is often the cause of abnormality. Also, when such a shorter-side opposite-ends type defect distribution as shown in FIG. 5C has occurred, a solution spray-related processing device is often the cause of abnormality. Based on these empirical facts, the user is allowed to easily judge whether or not the causal equipment unit candidate is really the cause of abnormality.

In addition, in the pattern classification areas 37, 38, 39, 40 and 41, a plurality of causal equipment unit candidates can be displayed in the 'equipment unit No.' field 34C. In the example of FIG. 4, three units of BBB-No. 4 unit, CCC-No. 4 unit, and AAA-No. 4 unit determined as causal equipment unit candidates by the causal equipment candidate determination section 15 are displayed in the pattern classification area 37. In this case, the display section 17 may be limited so as to display data relating only to causal equipment unit candidates satisfying a specified threshold value for the determination of causal equipment units out of the cause candidate equipment units determined by the causal equipment candidate determination section 15. That is, in that case, causal equipment unit candidates that do not satisfy the threshold value are determined as causal equipment units having low degrees of association, and omitted from display. Accordingly, the user is enabled to further promptly and easily narrow down causal equipment units that are really the cause of abnormality out of the causal equipment unit candidates determined by the system 1. It is noted that the master information storage section 13 shown in FIG. 1 is looked up for the threshold value.

The 'probability value (p-value)' field 35 is for displaying a probability value of a corresponding cause candidate equipment unit. This value is a probability value resulting when a cause candidate equipment unit is determined in the common path analysis performed by the causal equipment candidate determination section 15. This probability value also helps the user to narrow down causal equipment units candidate that are really the cause of abnormality out of the causal equipment unit candidates determined by the system 1.

Although the number of pattern classification areas (i.e., defect distribution patterns) to be displayed is five in the example of FIG. 4, yet it is not limited to this and may be increased or decreased. Besides, when all the classified defect distribution patterns cannot be displayed in one screen due to an areal restriction of the display screen, the pattern classification areas may be so designed as to be longitudinally scrolled and displayed.

The lower table area 92 contains a plurality of pages to be selected by tabs 71, 72, 73. This number of pages (i.e., number of tabs) is variably set so as to coincide with the number of causal equipment unit candidates listed in the pattern classification areas checked by the check field 31 of the upper table area 91. In the example of FIG. 4, since the number of cause candidate equipment units listed in the checked pattern classification area 37 is three, the number of pages is three.

Each page of the lower table area 92 is longitudinally segmented into a step and equipment unit display area 64, a 'unit No.' display area 65 for identifying an equipment unit, a 'substrate map superimposition' area 66 for displaying first and second defect distribution superimposed images in contrast, an 'estimated substrate count' display area 67, a 'processed substrate count' display area 68, and a '%' display area 69. Also, the page of the lower table area 92 is laterally segmented into an item display field 60, a first information display field 61 for displaying information as to determined causal equipment unit candidates, and a second information display field 62 for displaying information as to equipment units other than the causal equipment unit candidates in the same step as that executed by the causal equipment unit candidates.

In the step and equipment unit display area 64 are displayed step number, step name, unit number (No. unit) of a cause candidate equipment unit, and probability value in correspondence to the pattern classification area (i.e., defect distribution pattern) checked in the check field 31 of the upper table area 91 by the operator. In the example of FIG. 4, a step number "20000," a step name "photo step," a unit number (No. unit) of the causal equipment unit candidate "BBB-No. 4 unit," and a probability value "0.90" are displayed in the step and equipment unit display area 64. This is information corresponding to the first candidate, BBB-No. 4 unit, out of the three cause candidate equipment units, BBB-No. 4 unit, CCC-No. 4 unit, and AAA-No. 4 unit, listed in the pattern classification area 37 described above.

In the 'substrate map superimposition' area 66, a first defect distribution superimposed image resulting from superimposing, on one another, defect distributions on substrates processed by the cause candidate equipment unit is displayed in the first information display field 61. In contrast to this, second defect distribution superimposed images resulting from superimposing, on one another, defect distributions on substrates processed by equipment units other than the causal equipment unit candidate, respectively, in the same step as that executed by the causal equipment unit candidate are displayed in the second information display field 62.

This first defect distribution superimposed image or each second defect distribution superimposed image corresponds to a result of superimposing, on one another, defect distributions of substrates classified into one identical pattern classification area. In the example of FIG. 4, the first defect distribution superimposed image in the first information display field 61 is formed by superimposing, on one another, defect distributions of substrates subjected to the photo step 20000 by the BBB-No. 4 unit out of 30 substrates classified into the pattern classification area 37. Also, the second defect distribution superimposed images in the second information display field 62 are formed by superimposing, on one another, defect distributions of substrates subjected to the photo step 20000 by equipment units other than the BBB-No. 4 unit, i.e. BBB-No. 1 unit, BBB-No. 2 unit, BBB-No. 3 unit, BBB-No. 5 unit, BBB-No. 8 unit and BBB-No. 9 unit, on the one equipment-unit basis, out of 30 substrates classified into the pattern classification area 37.

As shown above, in the system 1, a first defect distribution superimposed image formed by superimposing, on one another, defect distributions on substrates processed by a causal equipment unit candidate, and second defect distribution superimposed images formed by superimposing, on one another, defect distributions on substrates processed by equipment units other than the causal equipment unit candidate in the same step as that executed by the causal equipment unit candidate, respectively, are displayed in contrast on one display screen 90. Accordingly, whether or not a causal equipment unit candidate determined by the system 1 is really the cause of abnormality can be grasped by the user intuitively through the sense of vision, and therefore judged more promptly and easily than it could conventionally. That is, it is unnecessary for the operator to redo the retrieval of in-line inspection information, production history information, or the like associated with the use of equipment units other than the causal equipment unit candidate each time, unlike the conventional case.

Also, the first defect distribution superimposed image in the first information display field 61 and the second defect distribution superimposed images in the second information display field 62 are formed and displayed on the one equipment-unit basis. Therefore, the user is enabled to further promptly and easily judge whether or not the causal equipment unit candidates determined by this system are really the cause of abnormality.

In addition, objects of which defect distributions are superimposed on one another may be not limited to substrates classified into one pattern classification area but expanded to all the substrates processed by the production line. That is, a first defect distribution superimposed image is formed by superimposing, on one another, defect distributions on substrates processed by a determined cause candidate equipment unit out of all the substrates processed by the production line. On the other hand, second defect distribution superimposed images are formed by superimposing, on one another, defect distributions on substrates processed by equipment units other than the causal equipment unit candidate, respectively, in the same step as that executed by the causal equipment unit candidate, out of all the substrates processed by the production line. In such a case, since objects of which defect distributions are superimposed on one another are increased, the user is enabled to more easily grasp the tendency of processing equipment units associated with a failure cause.

Also, in the 'estimated substrate count' display area 67 in FIG. 4, numbers of substrates of which defect distributions are superimposed on one another out of substrates classified into the same pattern classification area are displayed for each one of the equipment units displayed in the unit No. field 65. In the 'processed substrate count' display area 68, numbers of substrates processed by the equipment units displayed in the unit No. field 65 are displayed for each one of the equipment units. In the '%' display area 69, percentages of numbers of substrates classified into the same pattern classification area out of substrates processed by the equipment unit displayed in the unit No. field 65 are displayed. By this display, the user is enabled to judge whether or not the causal equipment unit candidate determined by the system 1 is really the cause of abnormality, not only intuitively but also numerically easily.

In this example, when the number of equipment units to be displayed in the second information display field 62 is so large that all the second defect distribution superimposed images associated with those processing equipment units cannot be displayed in one screen, the second information display field 62 can be laterally scrolled so that its contents can be displayed. The operator is allowed to scroll the contents of the second information display field 62 laterally by moving a scroll bar 70 with a mouse or the like.

As described before, a plurality of pages of the lower table area 92 can be changed over by the operator's selecting the tabs 71, 72, 73 with a mouse or the like. In the example of FIG. 4, when the operator selects the tab 71 corresponding to the first candidate, the page of cause candidate equipment unit "BBB-No. 4 unit" in the step number "20000" and the step name "photo step" is displayed. When the operator selects the tab 72 corresponding to the second candidate, the page of cause candidate equipment unit "CCC-No. 4 unit" in the step number "30000" and the step name "etching step" is displayed. Further, when the operator selects the tab 73 corresponding to the third candidate, the page of cause candidate equipment unit "AAA-No. 4 unit" in the step number "10000" and the step name "deposition step" is displayed. In such a case, for each of a plurality of cause candidate equipment units, a first defect distribution superimposed image formed by superimposing, on one another, defect distributions on substrates processed by the cause candidate equipment unit, and second defect distribution superimposed images formed by superimposing, on one another, defect distributions on substrates processed by equipment units other than the causal equipment unit candidate in the same step as that executed by the causal equipment unit candidate, can be displayed in contrast in a limited area of the display screen 90.

Also as described before, when the operator checks the check field 31 of one pattern classification area in the upper table area 91, information related to the checked pattern classification area (i.e., defect distribution pattern) is switchedly displayed in the lower table area 92 in linkage with the checking. For example, in the example of FIG. 4, as the pattern classification area 37 is checked, information related to the pattern classification area 37, i.e. the page of the cause candidate equipment unit "BBB-No. 4 unit" in the photo step that is the first candidate in the pattern classification area 37, or the like is displayed in the lower table area 92. In this case, if the operator checks the pattern classification area 38 instead of the pattern classification area 37, then information related to the pattern classification area 38, i.e. the page of the cause candidate equipment unit "BBB-No. 1 unit" in the photo step that is the first candidate in the pattern classification area 38, is displayed in the lower table area 92. In such a case, more information, especially differences in defect distributions of substrates among equipment units (unit differences), can be displayed in a limited area of the display screen 90. Therefore, the user is enabled to further promptly and easily judge whether or not a selected causal equipment unit candidate is really the cause of abnormality.

This embodiment has been described on an example in which the present invention is applied to a production line of thin film devices. However, the invention may also be widely applied to determine equipment units that have caused failure occurrence in a production line that executes one or more steps for substrates by using one or more units that can execute the individual steps, respectively. For instance, the invention may be applied also to production lines of semiconductor devices and the like.

The invention claimed is:

1. A failure-cause equipment determination system for determining an equipment unit that has caused failure occurrence in a production line in which one or more steps are executed on substrates by using one or more equipment units that can execute the individual steps, respectively, wherein
   the production line includes an inspection step for acquiring defect distribution information representing positions of defects on each of the substrates after an end of specified steps, the system comprising:
   a classification result acquisition section for classifying the substrates for each one of defect distribution patterns by using the defect distribution information as to the individual substrates;
   a causal equipment candidate determination section for determining causal equipment unit candidates that have caused failure occurrence out of the plurality of equipment units based on a classification result acquired by the classification result acquisition section and production history information for determining equipment units that have processed the substrates in the individual steps, respectively;
   a first defect distribution image forming section for forming a first defect distribution superimposed image by superimposing defect distributions on the individual substrates processed by the causal equipment unit candidates on one another;
   a second defect distribution image forming section for forming a second defect distribution superimposed image by superimposing, on one another, defect distributions on individual substrates processed by each of equipment units other than the causal equipment unit candidate in one same step as that executed by the causal equipment unit candidate; and
   a first display section for displaying the first defect distribution superimposed image and the second defect distribution superimposed images in contrast on one display screen.

2. The failure-cause equipment determination system as claimed in claim 1, further comprising:
   a third defect distribution image forming section for forming a third defect distribution superimposed image by superimposing, on one another, defect distributions on substrates classified into one defect distribution pattern; and
   a second display section for listing and displaying, for each one of the defect distribution patterns, a third defect distribution superimposed image corresponding to the defect distribution pattern, and causal equipment unit candidate information representing causal equipment unit candidates corresponding to the defect distribution pattern, together on the display screen.

3. The failure-cause equipment determination system as claimed in claim 2, wherein
   the second display section displays its display contents limitedly as to causal equipment unit candidates satisfying a specified threshold value for determination of causal equipment units out of the causal equipment unit candidates corresponding to the defect distribution pattern.

4. The failure-cause equipment determination system as claimed in claim 2, further comprising:
   an instruction input section for inputting an instruction to select one of causal equipment unit candidates of which causal equipment unit candidate information is displayed on the display screen, wherein
   the first display section, in linkage with a causal equipment unit candidate selected via the instruction input section, switches its display contents so as to display the first defect distribution superimposed image and the second defect distribution superimposed images as to the selected causal equipment unit candidate.

5. The failure-cause equipment determination system as claimed in claim 1, wherein
   the first and second defect distribution image forming sections form the first and second defect distribution superimposed images, respectively, for each one of the equipment units based on information for identifying the substrates and the production history information.

* * * * *